United States Patent
Tang et al.

(10) Patent No.: US 11,415,567 B2
(45) Date of Patent: Aug. 16, 2022

(54) METHOD FOR DETERMINING THE TRUE BOILING POINTS OF COMPLEX HYDROCARBON FLUIDS USING NUCLEAR MAGNETIC RESONANCE

(71) Applicant: SCHLUMBERGER TECHNOLOGY CORPORATION, Sugar Land, TX (US)

(72) Inventors: Yiqiao Tang, Allston, MA (US); Yi-Qiao Song, Newton Center, MA (US); Sharath Chandra Mahavadi, Lexington, MA (US); Ravinath Kausik Kadayam Viswanathan, Sharon, MA (US); Shawn David Taylor, Reading, MA (US); Gary Potten, Spring, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 23 days.

(21) Appl. No.: 16/977,691

(22) PCT Filed: Mar. 5, 2019

(86) PCT No.: PCT/US2019/020760
§ 371 (c)(1),
(2) Date: Sep. 2, 2020

(87) PCT Pub. No.: WO2019/173344
PCT Pub. Date: Sep. 12, 2019

(65) Prior Publication Data
US 2021/0041414 A1  Feb. 11, 2021

Related U.S. Application Data

(60) Provisional application No. 62/639,266, filed on Mar. 6, 2018.

(51) Int. Cl.
G01N 33/28 (2006.01)
G01N 24/08 (2006.01)
G01R 33/44 (2006.01)

(52) U.S. Cl.
CPC ....... G01N 33/2823 (2013.01); G01N 24/081 (2013.01); G01R 33/448 (2013.01)

(58) Field of Classification Search
CPC . G01N 24/081; G01N 24/2823; G01R 33/448
See application file for complete search history.

(56) References Cited

U.S. PATENT DOCUMENTS 7,718,434 B2    5/2010  Freed
2010/0049681 A1  2/2010  Pradhan et al.
(Continued)

FOREIGN PATENT DOCUMENTS

WO    2017100000 A2   6/2017

OTHER PUBLICATIONS

Green, L. E., L. J. Schmauch, and J. C. Worman. "Simulated Distillation by Gas Chromatography" Analytical chemistry 36.8 (1964): 1512-1516.
(Continued)

*Primary Examiner* — Gregory H Curran
(74) *Attorney, Agent, or Firm* — Trevor G. Grove (57) ABSTRACT

Nuclear magnetic resonance (NMR) relaxation and/or diffusion measurements are used to deduce fluid compositional information such as a chain-length distribution, which may then be used to predict the true boiling points (TBP) of a sample of a complex hydrocarbon fluid mixture, such as a crude oil. The NMR measurements may be considered a fast and portable proxy measurement in estimating fluid TBP distributions in lieu of distillation methods, or the simulated distillation by gas chromatography.

20 Claims, 9 Drawing Sheets

(56) References Cited

U.S. PATENT DOCUMENTS

2013/0103627 A1    4/2013  Maddinelli et al.
2015/0268323 A1    9/2015  Song et al.
2018/0011037 A1*   1/2018  Koseoglu .......... G01R 33/4625

OTHER PUBLICATIONS

Worman, J C., and L. E. Green. "Simulated distillation of high boiling petroleum fractions " Analytical Chemistry 37.12 (1965): 1620-1621.

Freed, Denise E., Lauren Burcaw, and Yi-Qiao Song. "Scaling laws for diffusion coefficients in mixtures of alkanes." Physical review letters 94.6 (2005): 067602.

Freed, Denise E. "Dependence on chain length of NMR relaxation times in mixtures of alkanes." The Journal of chemical physics 126.17 (2007): 174502.

Hürlimann, M. D., et al. "Hydrocarbon composition from NMR diffusion and relaxation data." Petrophysics 50.02 (2009).

Barbosa, Lúcio L., et al. "Relative hydrogen index as a fast method for the simultaneous determination of physicochemical properties of petroleum fractions." Fuel 210 (2017): 41-48.

Orr, Mark JL. "Introduction to radial basis function networks." Centre for Cognative Science, (1996), 67 pages.

Ha, Dongwan, et al. "Scalable NMR spectroscopy with semiconductor chips" Proceedings of the National Academy of Sciences 111.33 (2014): 11955-11960.

Hürlimann, M D., et al., "Quantitative measurement of two-dimensional distribution functions of diffusion and relaxation in grossly inhomogeneous fields." Journal of Magnetic Resonance 157.1 pp. 31-42 (2002).

Barbosa et al., "Low-field nuclear magnetic resonance for petroleum distillate characterization", Fuel Processing Technology, May 2015, No. 138, pp. 202-208.

* cited by examiner

METHOD FOR DETERMINING THE TRUE BOILING POINTS OF COMPLEX HYDROCARBON FLUIDS USING NUCLEAR MAGNETIC RESONANCE

CROSSS REFERENCE TO RELATED APPLICATIONS

This application claims priority to and the benefit of U.S. Application No. 62/639,266, which was filed on Mar. 6, 2018, the entirety of which is incorporated herein by reference.

FIELD

This disclosure relates to the hydrocarbon industry. More particularly this disclosure relates to methods for using NMR relaxation and/or NMR diffusion measurements to predict true boiling points ("TBP") of complex hydrocarbon fluid mixtures, such as crude oils.

BACKGROUND

Conventionally, the boiling range of a crude sample is determined by a precise analytical distillation, commonly called true boiling point (TBP) distillation. The distribution of true boiling points (TBP) is a common approach to describe the composition of the crude oil, its fractions (e.g. diesel, gas-oil, etc.), and derivatives (e.g. blends). TBP is extensively used as a key input for petroleum thermodynamic modeling to predict refining product qualities and quantities from crude petroleum and has been traditionally determined by analytical distillation. In fact, the obtained data reveal potential economic value of a petroleum stock, and have been used extensively for process design, pilot plant studies, and control of manufacturing processes. However, the prolonged measurement time and hardware requirements forbid a wide field deployment of the technology.

Figure 1:
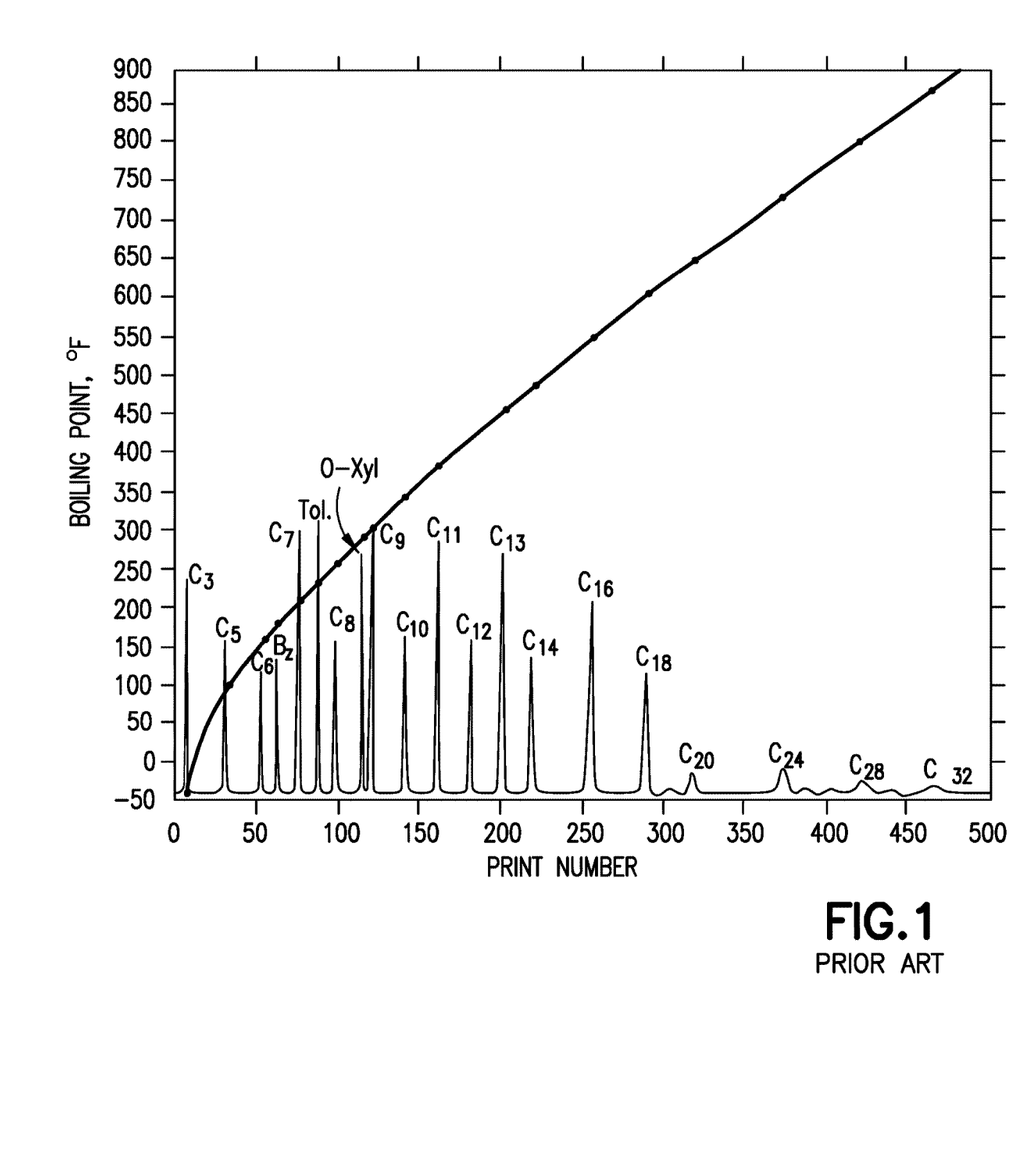
FIG. 1 shows a graph depicting the determination of a calibration curve.
Figure 2:
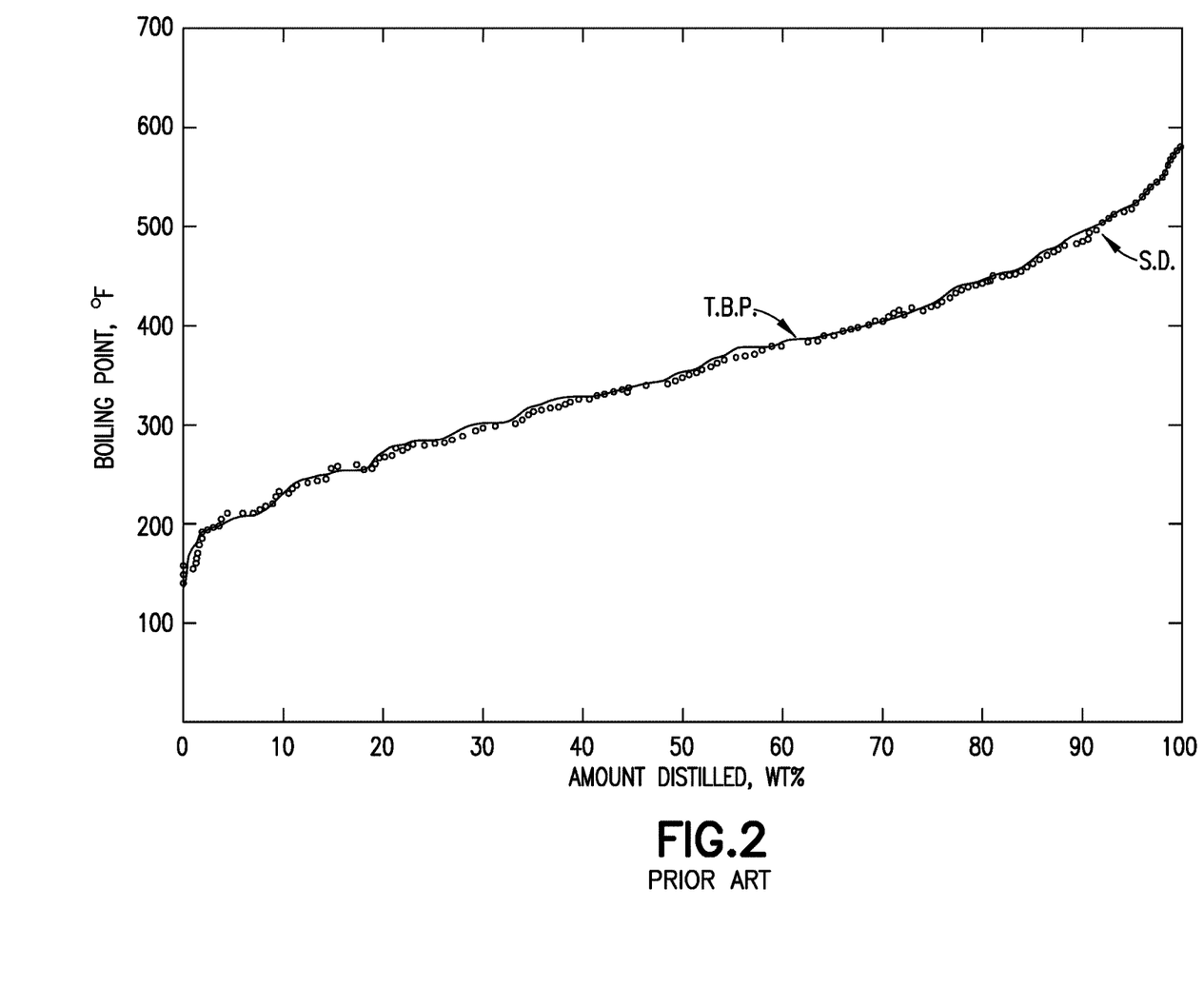
FIG. 2 shows a graph depicting the correlation between TBP distillation and GC methods on a crude oil sample.

Over the years, gas chromatography has been developed as a valid and much more rapid approximation of measuring TBP of crude oils, its fractions, and derivatives. See, e.g., Green, L. E. et al., "Simulated Distillation by Gas Chromatography", *Analytical Chemistry* 36.8 pp. 1512-1516 (1964); Worman, J. C. et al., "Simulated Distillation of High Boiling Petroleum Fractions", *Analytical Chemistry*, 37.12 pp. 1620-1621 (1965). As shown in prior art FIG. 1, a calibration curve can be obtained by performing GC on a set of hydrocarbon compounds with known boiling points. The calibration curve may then be used to further deduce boiling points of unknown samples, based on their GC results as suggested in prior art FIG. 2.

Despite significant improvements over the distillation method in terms of turn-around time and sample volume requirements, GC is not a viable method to determine the full range of TBP for hydrocarbon liquid mixtures for rapid and portable or on-line measurements.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In an embodiment, a method for determining a boiling point distribution of a sample of hydrocarbon fluid is described. The method includes: using a nuclear magnetic resonance (NMR) system, applying an (NMR) signal to the sample and measuring at least one of a resulting translational diffusion signal and a resulting spin relaxation signal; determining at least one of an NMR translational diffusion distribution and an NMR relaxation time distribution from the at least one of a resulting translational diffusion signal and a resulting spin relaxation signal; and determining a boiling point distribution for the hydrocarbon fluid based upon the at least one of an NMR translational diffusion and NMR spin relaxation distribution.

In a further embodiment, a method for determining a boiling point distribution of a hydrocarbon fluid is described. The method includes: obtaining a sample of the hydrocarbon fluid at a rig site, a transportation pipeline, or a refinery facility; using an nuclear magnetic resonance (NMR) system, applying an (NMR) signal to the sample and measuring at least one of a resulting translational diffusion signal and a resulting spin relaxation signal; determining at least one of an NMR translational diffusion distribution and an NMR decay distribution from the at least one of a resulting translational diffusion signal and a resulting spin relaxation signal; and determining a hydrocarbon fluid chain length distribution from the at least one of the NMR translational diffusion distribution and NMR decay distribution; relating the hydrocarbon fluid chain length distribution to a hydrocarbon fluid molecular weight distribution; and determining a boiling point distribution for the hydrocarbon fluid by relating the hydrocarbon fluid molecular weight distribution to the boiling point distribution.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

As previously suggested, the distribution of true boiling points (TBP) is a common approach to describe the composition of crude oil, its fractions (e.g. diesel, gas-oil, etc.), and derivatives (e.g. blends). TBP is extensively used as a key input for petroleum thermodynamic modeling to predict refining product qualities and quantities from crude petroleum and has been traditionally determined by analytical distillation. Also, as previously suggested, gas chromatography has been developed as a valid and much more rapid approximation of measuring TBP of crude oils, its fractions, and derivatives. Even so, GC is not a viable method to determine the full range of TBP for hydrocarbon liquid mixtures for rapid and portable or on-line measurements as it requires very expensive equipment and is not rapid enough for many applications.

According to one aspect, NMR relaxation and/or diffusion measurements are used to deduce fluid compositional information, which are then used to predict the true boiling points of complex hydrocarbon fluid mixtures, such as crude oils. The NMR measurements may be considered a fast and portable proxy measurement for GC in estimating fluid TBP distributions. In one aspect, boiling point distributions may be expressed in terms of the measured boiling point temperatures or the carbon number series or distribution (e.g. chain length of the n-paraffin series of hydrocarbons) with the equivalent boiling point values.

When applied to the oilfield, NMR mainly studies hydrogen spins in fluids, which when subject to an external static magnetic field embody two distinctive energy levels with a small gap $\Delta E$. Upon applying an AC magnetic field at frequency $f=\Delta E/h$ (where h is the Planck's constant) for a definite time, a spin resonance is created, and an excited NMR signal is generated. The resonance condition may be further controlled through a series of AC and DC magnetic-field pulses in the time domain. For a specific time-sequence of AC/DC pulses, the evolution of the resulting NMR signal relates to certain fluid characteristics.

NMR investigates fluid dynamics at a molecular level, and therefore is intrinsically sensitive to molecular motions of all sorts (vibration, rotation, and translational movement for example). Particularly, at the operating frequency of a few to tens of MHz, NMR methods probe translational and rotational motions of molecules. The motion of a molecule is dictated by the size of the molecule itself and its surrounding fluids. Therefore, by measuring molecular motions, NMR provides insights into the composition of the fluid, and in particular to the size distribution of the fluid species in a fluid mixture. See, Freed, Denise E. et al., "Scaling Laws for Diffusion Coefficients in Mixtures of Alkanes", "*Physical Review Letters,* 94.6 (2005): 067602; Freed, Denise E. et al., "Dependence on chain Length of NMR Relaxation Times in Mixtures of Alkanes," *The Journal of Chemical Physics,* 126.17 (2007): 174502" and Hurlimann, M. D. et al., "Hydrocarbon Composition from NMR Diffusion and Relaxation Data", Petrophysics, 50.02 (2009). Also, see U.S. Pat. No. 7,718,434 to Freed, entitled "Method for Determining the characteristics of Crude Oils and Mixtures of chain Molecules by Diffusion and Relaxation Measurements, the contents of which are herein incorporated by reference in its entirety. As described hereinafter, this size distribution can be used to deduce a corresponding TBP distribution of the fluid.

Figure 3A:
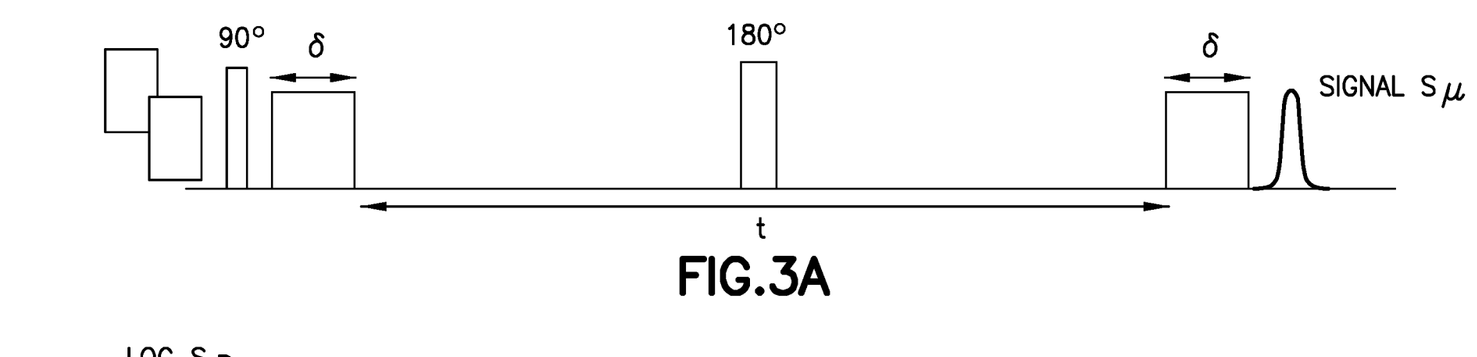
FIG. 3A shows the timing sequence of a pulse-field gradient (PFG) nuclear magnetic resonance (NMR) experiment.
Figure 3B:
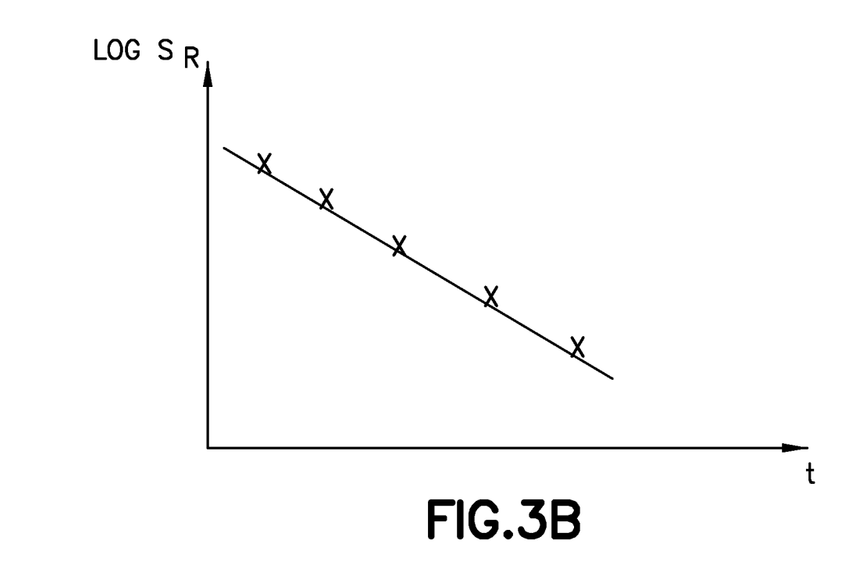
FIG. 3B shows a plot of a log of signal amplitude as a function of τ, from which translation diffusion of fluid molecules may be deduced.
Figure 3C:
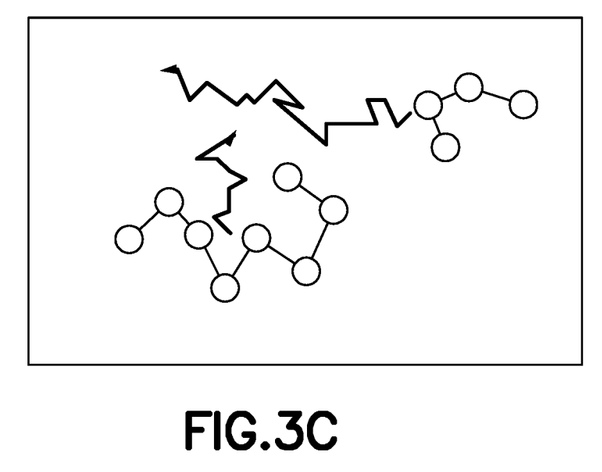
FIG. 3C depicts two hydrocarbon molecules undergoing translational movement with the traces representing trajectories of the respective centers of mass in time lapse.

According to embodiments, two types of NMR measurements may be used to deduce molecular size distribution. The first is measuring fluid translational diffusion coefficients, $D_T$, in pulsed field gradient (PFG) experiments. As shown in FIG. 3A, two AC pulses of 90° and 180° are interleaved by two DC pulses of duration $\delta$ which are located time $\tau$ apart. The generated or resulting NMR signal is denoted by $S_R$. The basic idea is that the original NMR signal is "sabotaged" and "recovered" by the application of the pair of DC pulses. The recovered signal is attenuated by molecular diffusion (translational movement of the hydrocarbon molecules—as seen in FIG. 3c) through the time period, $\tau$, in between the two DC pulses. For bulk fluid, the recovered signal, $S_R$, is a function of $\tau$ and $D_T$ according to $S_R = e^{-b\tau D_T}$, where b is a constant. By studying (or plotting) $S_R$ as a function of $\tau$ (as seen in FIG. 3b), $D_T$ can be quantitatively determined.

Embodiments of the present disclosure may obtain a molecular diffusion distribution coefficient, which can be further used as hereinafter described to deduce molecular size distributions. Quantitatively, a scaling law was developed that relates a coefficient, $D_i$, to the effective chain length, $N_i$, of individual fluid components. The theory shows that in a complex fluid mixture, the diffusion coefficient of a component ($D_i$) scales with its chain length to the power v according to:

$$D_i = [A(T,p) \langle N \rangle^{-\beta(T,p)}] N_i^{-\nu} \qquad (1)$$

where $\langle N \rangle$ is the weighted average chain size of all molecules in the sample, A and $\beta$ are known coefficients which are a function of temperature T and pressure p, and the exponent v is independent of temperature and pressure, and for a mixture of alkanes was found to be 0.7. For crude oils, equation (1) may be used to infer the chain length distribution $N_i$ from the measured distribution of diffusion coefficients, given that A, $\beta$, and v are known a priori.

Figure 4:
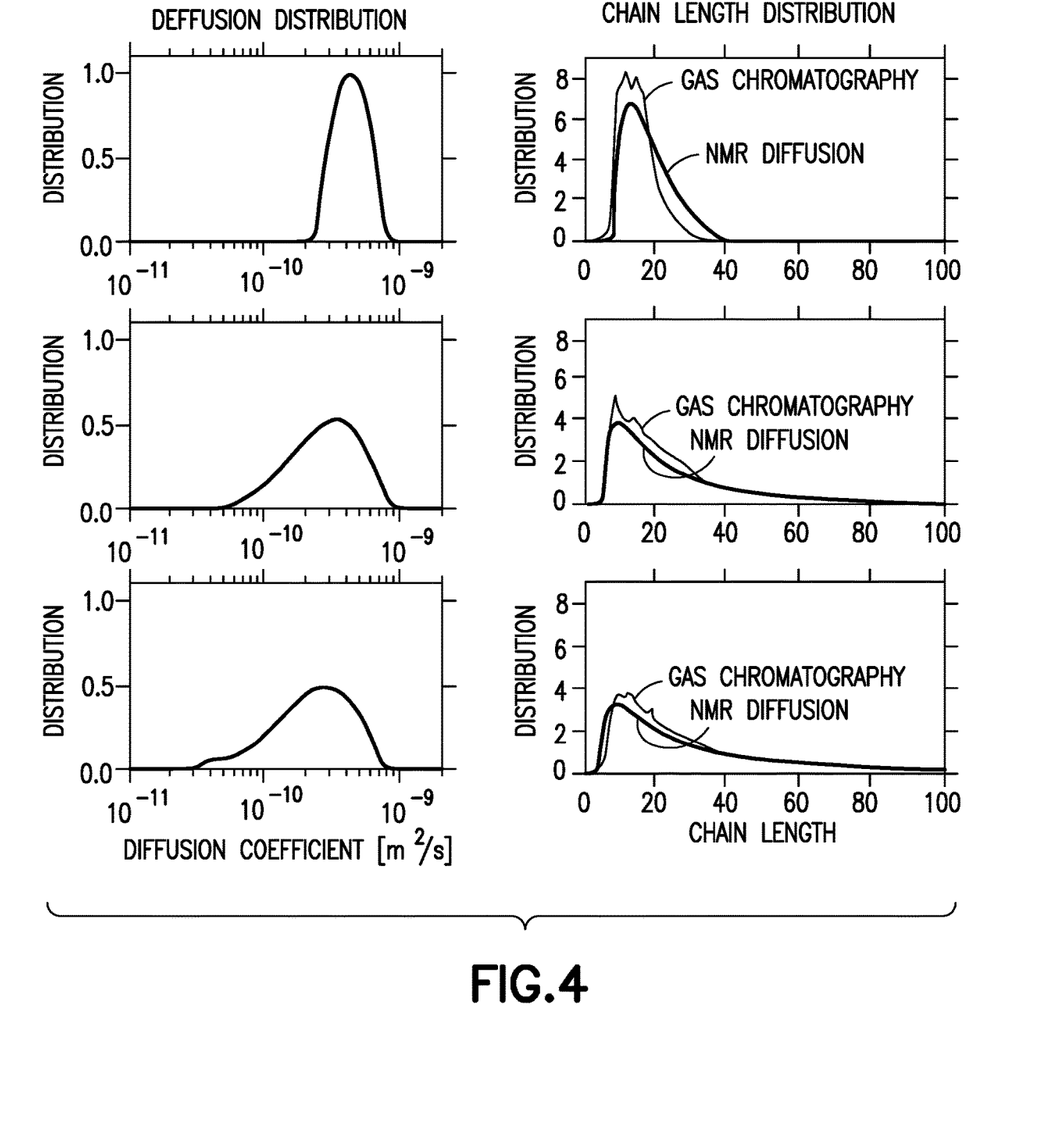
FIG. 4 shows estimates of chain length distribution from NMR diffusion measurements with the panels on the left showing the diffusion distributions measured by NMR for different oils and the panels on the right showing the comparisons of the deduced chain length distribution obtained through the NMR measurements with gas chromatography data.

The left three plots of FIG. 4 show the measured NMR diffusion distribution for three different crude oils. The right three plots show the chain length distribution estimated from the measured diffusion coefficients for three different crude oils (by using equation (1). As seen in FIG. 4, all three chain length calculations made based on the NMR diffusion measurements agree well with standard lab GC measurements.

Figure 5A:
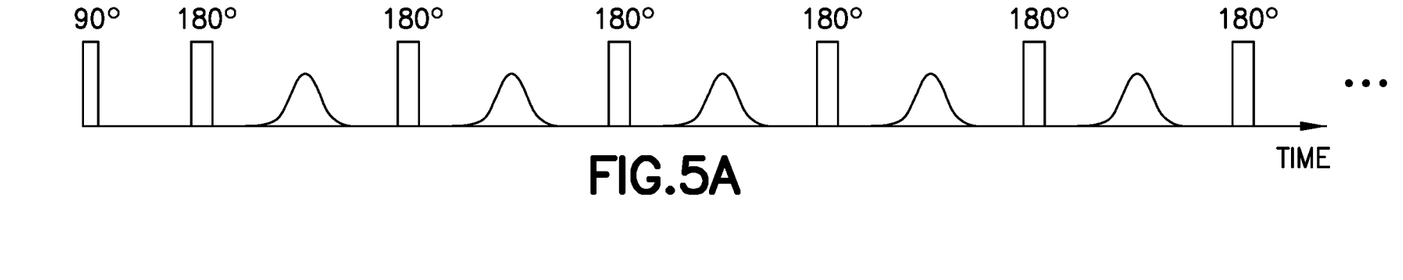
FIG. 5A shows the timing sequence of an NMR CPMG experiment.
Figure 5B:
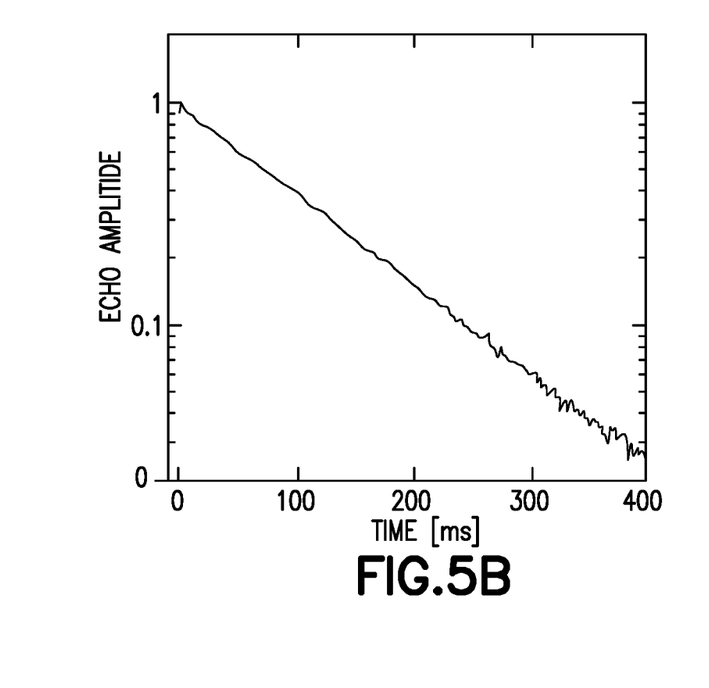
FIG. 5B shows a plot of the log of signal amplitude as a function of accumulative experiment time.
Figure 5C:
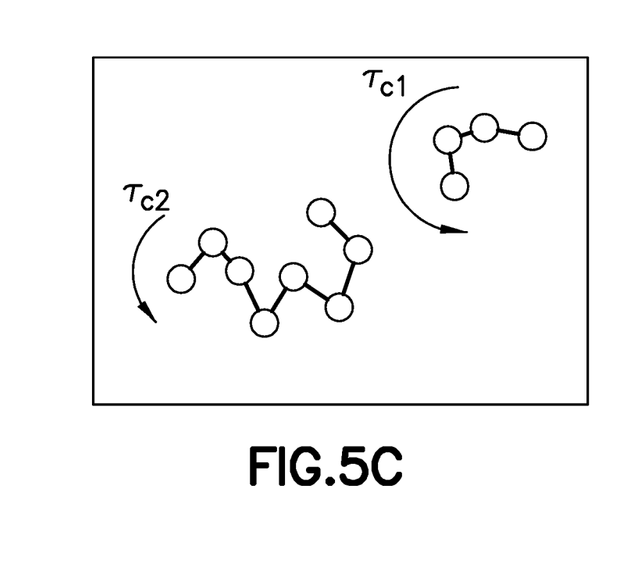
FIG. 5C shows a depiction of the orientational fluctuation of two hydrocarbon molecules.

According to another embodiment, a second type of NMR method that may be used for deducing chain length distribution measures the rate at which the excited NMR signal diminishes, during which the fluid ensemble restores to its state of thermal equilibrium. This process is called "relaxation". The pulse sequence for an NMR relaxation measurement is seen in FIG. 5a, where 90° and 180° AC pulses are utilized, typically according to a CPMG (Carr-Purcell-Meiboom-Gill) technique, and echo signals are recorded between the 180° pulses. The AC pulses are typically about 10 microseconds in duration, and a typical pulse train consists of hundreds and even a few thousand of such pulses. It should be appreciated that NMR relaxation happens through interaction of the spin system with its surrounding thermal bath. The main relaxation mechanism for proton spins in a hydrocarbon fluid is the nuclear spin-spin interaction within molecules. The relaxation or decay of the amplitude of the recorded echoes over time provides what is called a $T_2$ measurement as seen in FIG. 5b. This mechanism originates from the tumbling of molecules by thermal agitation, through which relative orientations between each spin momentum pairs fluctuate, as shown in FIG. 5C.

Figure 6:
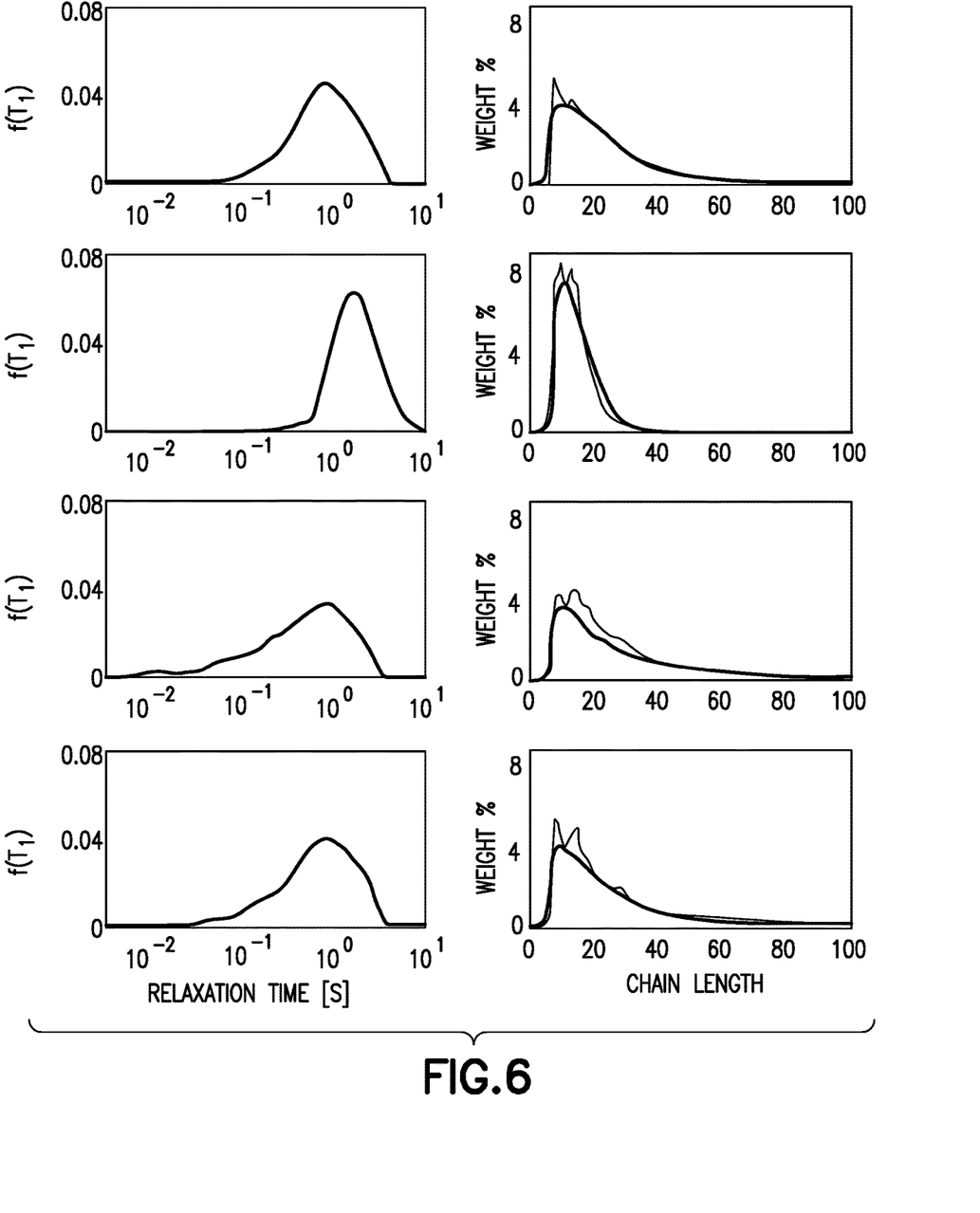
FIG. 6 shows estimates of chain length distribution obtained from the NMR relaxation measurement with the panels on the left showing T2 distributions measured by NMR for different oils and the panels on the right showing the comparisons of the deduced chain length distribution obtained through the NMR measurements with gas chromatography data.

A characteristic time scale of the fluctuation correlation may be designated by a single parameter, $\tau_c$, which ties to molecular size and its surroundings. Similar to the diffusion measurement, a relation between chain length and relaxation times can be developed in hydrocarbon fluids. To a good approximation, the $T_2$ and $T_1$ of a fluid component, i, relates to the effective chain length of that component, $N_i$, by $$T_{1/2,i} = [B(T, p)\langle N \rangle^{-\gamma(T,p)}] N_i^{-\kappa} \quad (2)$$

where B and γ are known coefficients, which are a function of temperature T and pressure p, and the exponent κ is a constant taken to be 1.3±0.15. The left panels of FIG. 6 show the $T_1$ distributions of four crude oils, while the right panels of FIG. 6 show the excellent agreement on chain length distribution determinations made for the four crude oils using GC and using $T_1$ measurements and applying equation (2).

According to one aspect, where it is desired to obtain a $T_1$ relaxation time measurement in lieu of or in addition to a $T_2$ measurement, the pulse sequence of the NMR equipment is adjusted accordingly.

For a fluid sample mainly comprising alkanes, the following relationship correlates chain length N of a component (i) to molecular weight, MW of that component:

$$MW = (N \times 14) + 2. \quad (3)$$

Where a fluid sample includes aromatic compounds as well as alkanes, equation (3) may be modified to:

$$MW = \sigma(14N+2) + (1-\sigma)(13N) \quad (3a)$$

where σ is the weight fraction of alkanes in the hydrocarbon fluid sample.

In one embodiment, the weight fraction of alkanes is determined by plotting a diffusion (D)–$T_2$ correlation spectrum (i.e., a DT2 plot) for the complex fluid. See, Hürlimann, M. D., et al., "Quantitative measurement two-dimensional distribution functions of diffusion and relaxation in grossly inhomogeneous fields." *Journal of Magnetic Resonance* 157.1 pp. 31-42 (2002). The value of σ is then determined according to $$\sigma = (K_{al} - K)/(K_{al} - K_{ar}) \quad (3b)$$

where K is the slope of the DT2 plot, $K_{al}$=0.7 is the slope of a DT2 plot for alkane (aliphatic) compounds, and $K_{ar}$=0.5 is the slope of a DT2 plot for aromatic compounds and/or may be experimentally determined.

In addition, a large body of literature present numerous correlation functions among fluid properties. See, e.g., Barbosa, L. L. et al., "Relative hydrogen index as a fast method for the simultaneous determination of physicochemical properties of petroleum fractions." *Fuel* 210 pp. 41-48 (2017). Of particular relevance is:

$$MW = 42.965 \exp(2.097 \times 10^{-4} BP - 7.78712 SG + 2.08476 \times 10^{-3} BPSG) BP^{1.26007} SG^{4.98308} \quad (4)$$

where MW is molecular weight, and BP and SG are respectively average boiling point temperature (in ° K.) and specific gravity of the corresponding oil fraction. Other relationships of relevance include:

$$°API = \left(\frac{141.5}{SG}\right) - 131.5 \quad (5)$$

$$°API = (17.2 \pm 0.6) RHI^{4.6 \pm 0.1} \quad (6)$$

$$MW = (46 \pm 2) \times 10^1 RHI^{-4.9 \pm 0.3}. \quad (7)$$

From equation (5)-(7), a derivation may be established from specific gravity SG to molecular weight MW according to:

$$SG = \frac{141.5}{(5443 \times MW^{-0.939} + 131.5)} \quad (8)$$

Combining equations (4) and (8), a derivation from MW to BP is derived according to:

$$MW = 42.965 \quad (9)$$
$$\exp\left(2.097 \times 10^{-4} BP - 7.78712\left[\frac{141.5}{(5443 \times MW^{-0.939} + 131.5)}\right] + 2.08476 \times 10^{-3} BP\left[\frac{141.5}{(5443 \times MW^{-0.939} + 131.5)}\right]\right)$$
$$BP^{1.26007}\left[\frac{141.5}{(5443 + MW^{-0.939} + 131.5)}\right]^{4.98308}$$

Figure 7A:
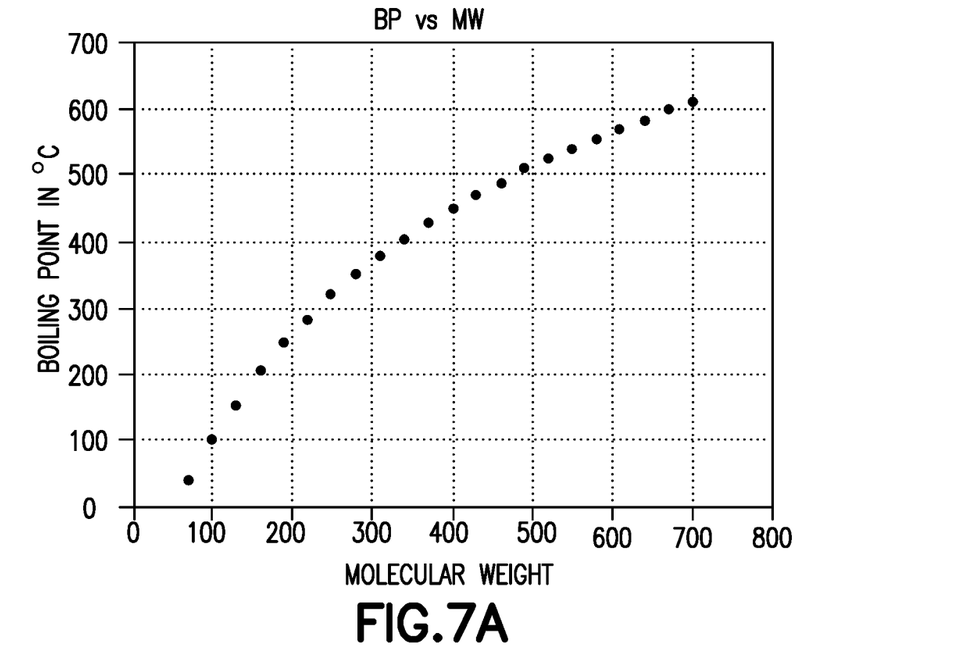
FIG. 7A depicts calculated boiling point (BP) vs. molecular weight (MW) correlation using equation (9)
Figure 7B:
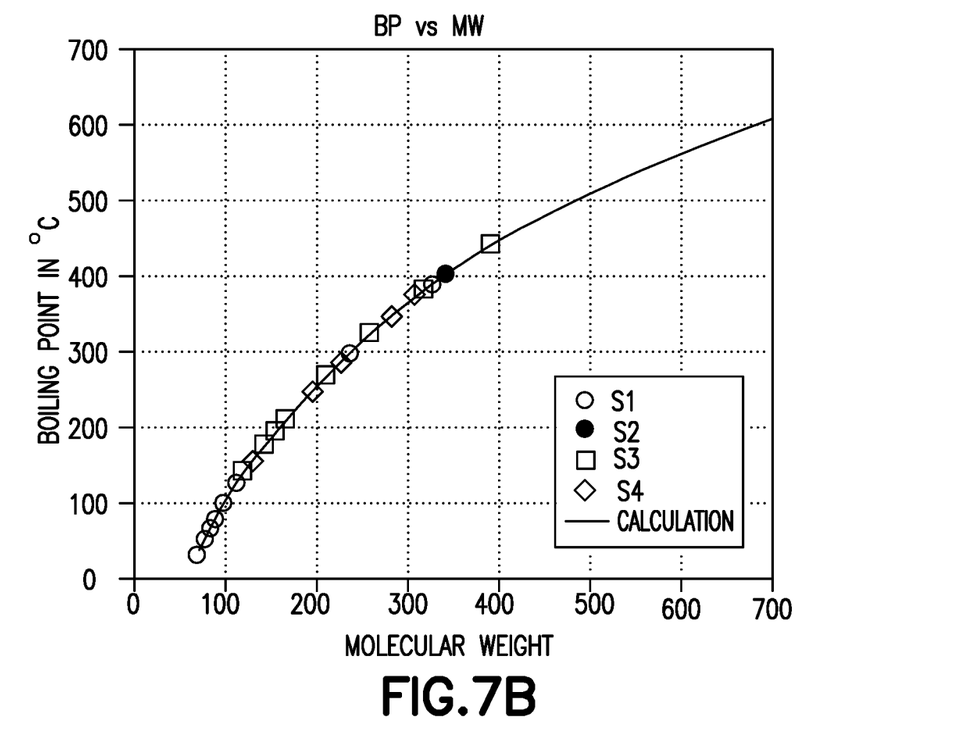
FIG. 7B depicts a calculated BP vs MW correlation.

FIG. 7A shows the calculated boiling point as a function of molecular weight as determined according to equation 9. FIG. 7B shows calculated molecular weight as a function of boiling point and specific gravity using equation (4) overlaid with data points for four oil samples whose boiling points and molecular weight were known. A good agreement is obtained.

Figure 8A:
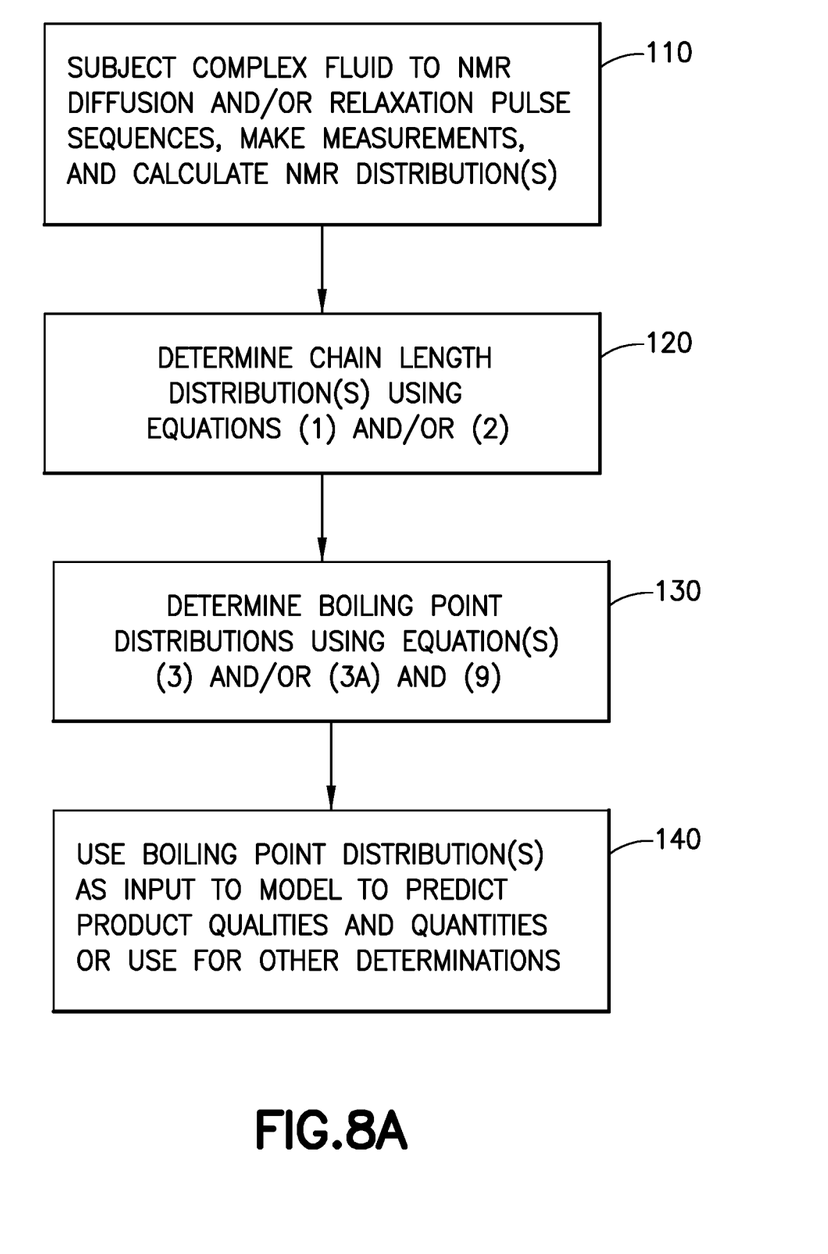
FIG. 8A shows a workflow in obtaining TBP distributions from NMR relaxation and/or diffusion spectra.

Based on the above, a boiling point distribution of a complex hydrocarbon fluid is obtained using a workflow as shown in FIG. 8A. In particular at 110, NMR diffusion and/or NMR relaxation measurement(s) are obtained by subjecting the fluid to an NMR system that provides NMR pulses, makes NMR measurements, and calculates one or more distributions of diffusion and/or relaxation values (seen in the left panel of FIG. 8B where distributions of $T_1$ and $T_2$ values are shown for an oil sample). The calculations may be made with one or more processors that are part of the NMR system, or with processors that receive the NMR measurements from the NMR system. At 120, a distribution (f) of chain lengths is determined via equations (1) and/or (2) using the NMR values obtained at 110 (as seen in the middle panel of FIG. 8B where chain length distributions for $T_1$ and $T_2$ values using equation (2) are shown plotted relative to GC values (GC1 relating to chain lengths of 1 to 36 and GC2 relating to chain lengths of 10 to 60. At 130, the chain length distribution is then converted to a boiling point distribution by using equation (3) to equate chain lengths to molecular weights and equation (9) to obtain boiling points from the molecular weights. The boiling point distribution is shown in the right panel of FIG. 8B where percent yield is plotted against boiling point temperature to provide a volume percentage curve and a weight percentage curve. The conversion made at 130 is performed by one or more processors. At 140, the boiling point distribution is optionally used as an input to a petroleum thermodynamic model implemented in one or more processors in order to predict refining product qualities and quantities from the crude petroleum (complex hydrocarbon fluid), or for other determinations.

It will be appreciated that both NMR diffusion and NMR relaxation measurements may be made, and separate boiling point distributions may be made based on each. In most cases the boiling point distribution determinations will be substantially similar. In one embodiment, where they differ, an average of the two may be taken, although if it is found that the crude oil contains hydrocarbons primarily having only one or two carbons, the NMR diffusion measurements may be selected for use as opposed to the relaxation measurements.

Figure 8B:
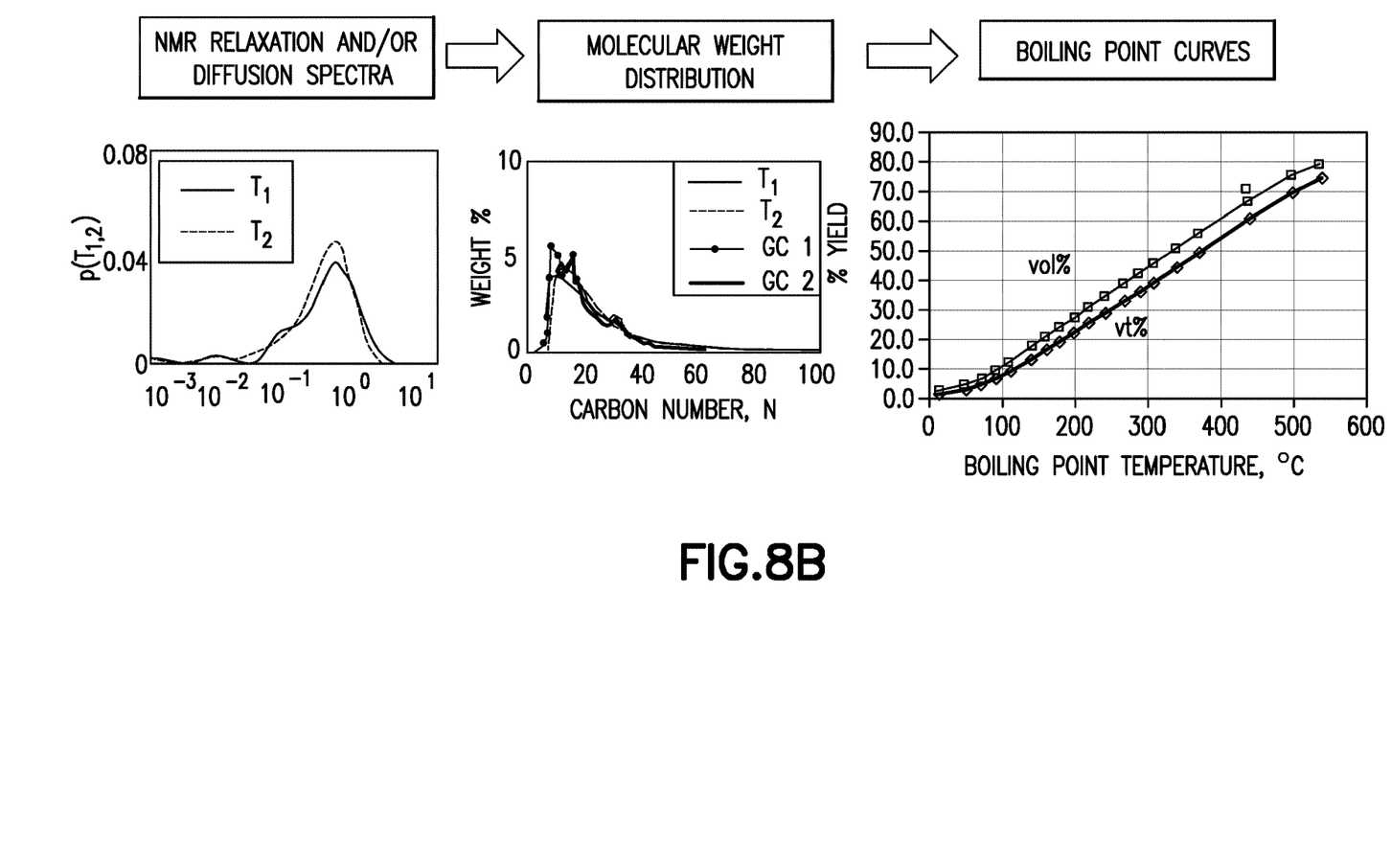
FIG. 8B shows the work products of the workflow of FIG. 8A.

Given the close agreement between NMR and GC (as seen in FIGS. 4, 6, and 8B) on a wide range of tested petroleum mixtures, according to one aspect, embodiments of the present disclosure may use NMR as a fast proxy method for determining BP distribution of fluids. An advantage of NMR over GC is the measurement speed. For example, a typical relaxation measurement only takes 10 seconds to conduct whereas a typical GC experiment will typically take 10 minutes to conduct. In addition, as recent advances in NMR hardware has permitted the NMR hardware to be scaled down dramatically, allowing field deployment in a miniaturized footprint, the shortened measurement time and its portable form factor will enable an NMR-based online monitoring of TBP in an oil production environment; e.g., at rig sites, in the transportation pipelines, and at the refinery facilities.

Some of the methods and processes described above can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although a few example embodiments have been described in detail above, those skilled in the art will readily appreciate that many modifications are possible in the example embodiments without materially departing from the scope of the present disclosure, described herein. Accordingly, such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for determining a boiling point distribution of a sample of hydrocarbon fluid comprising:
   using a nuclear magnetic resonance (NMR) system, applying an (NMR) signal to the sample and measuring at least one of a resulting translational diffusion signal and a resulting spin relaxation signal;
   determining at least one of an NMR translational diffusion distribution and an NMR relaxation time distribution from the at least one of a resulting translational diffusion signal and a resulting spin relaxation signal; and
   determining a boiling point distribution for the hydrocarbon fluid based upon the at least one of an NMR translational diffusion and NMR spin relaxation distribution, wherein said determining a boiling point distribution comprises determining a hydrocarbon fluid chain length distribution from the at least one of the NMR translational diffusion distribution and NMR relaxation time distribution, relating the hydrocarbon fluid chain length distribution to a hydrocarbon fluid molecular weight distribution, and relating the hydrocarbon fluid molecular weight distribution to the boiling point distribution.

2. The method according to claim 1, wherein said determining a hydrocarbon fluid chain length distribution comprises solving $D_i = [A(T,p) \langle N \rangle^{-\beta(T,p)}] N_i^{-\nu}$ for $N_i$, where $N_i$ is said hydrocarbon fluid chain length distribution, $D_i$ is said NMR translational diffusion distribution, $\langle N \rangle$ is a weighted average chain size of all molecules in the sample, A and $\beta$ are known coefficients which are a function of temperature T and pressure p, and the exponent v is a constant.

3. The method according to claim 2, wherein v is equal to 0.7.

4. The method according to claim 1, wherein said determining a hydrocarbon fluid chain length distribution comprises solving $T_{,i} = [B(T,p) \langle N \rangle^{-\gamma(T,p)}] N_i^{-\kappa}$ for $N_i$, where $N_i$ is said hydrocarbon fluid chain length distribution, $T_{,i}$ is said NMR decay distribution, B and $\gamma$ are known coefficients which are a function of temperature T and pressure p, and the exponent $\kappa$ is a constant.

5. The method according to claim 4, wherein $T_{,i}$ is a $T_{2,i}$ NMR decay distribution.

6. The method according to claim 5, wherein $T_{,i}$ is a $T_{1,i}$ NMR decay distribution.

7. The method according to claim 5, wherein K is a constant set in a range equal to 1.3±0.15.

8. The method according to claim 1, wherein said relating the hydrocarbon fluid chain length distribution to a hydrocarbon fluid molecular weight distribution comprises solving for at least one of MW=(N×14)+2 and MW=$\sigma$(14N+2)+(1−$\sigma$) (13N) where MW is a molecular weight of a hydrocarbon fluid molecule, N is a hydrocarbon fluid chain length of that hydrocarbon fluid molecule, and $\sigma$ is the weight fraction of alkanes in the hydrocarbon fluid sample.

9. The method according to claim 8, wherein said relating the hydrocarbon fluid molecular weight distribution to the boiling point distribution comprises solving for $$MW = 42.965 \exp(2.097 \times 10^{-4} BP - 7.78712) \left[\frac{141.5}{(5443 \times MW^{-0.939} + 131.5)}\right] + 2.08476 \times 10^{-3} BP \left[\frac{141.5}{(5443 \times MW^{-0.939} + 131.5)}\right] + BP^{1.26007}\left[\frac{141.5}{(5443 + MW^{-0.939} + 131.5)}\right]^{4.98308}$$

where BP is the boiling point of a hydrocarbon fluid fraction of molecular weight MW.

10. The method according to claim 2, wherein said relating the hydrocarbon fluid chain length distribution to a hydrocarbon fluid molecular weight distribution comprises solving for at least one of MW=(N×14)+2 and MW=$\sigma$(14N+2)+(1−$\sigma$) (13N) where MW is a molecular weight of a hydrocarbon fluid molecule, N is a hydrocarbon fluid chain length of that hydrocarbon fluid molecule, and $\sigma$ is the weight fraction of alkanes in the hydrocarbon fluid sample.

11. The method according to claim 10, wherein said relating the hydrocarbon fluid molecular weight distribution to the boiling point distribution comprises solving for $$MW = 42.965 \exp(2.097 \times 10^{-4} BP - 7.78712) \left[\frac{141.5}{(5443 \times MW^{-0.939} + 131.5)}\right] + 2.08476 \times 10^{-3} BP \left[\frac{141.5}{(5443 \times MW^{-0.939} + 131.5)}\right] + BP^{1.26007}\left[\frac{141.5}{(5443 + MW^{-0.939} + 131.5)}\right]^{4.98308}$$

where BP is the boiling point of a hydrocarbon fluid molecule of molecular weight MW.

12. The method according to claim 4, in said relating the hydrocarbon fluid chain length distribution to a hydrocarbon fluid molecular weight distribution comprises solving for at least one of MW=(N×14)+2 and MW=$\sigma$(14N+2)+(1−$\sigma$) (13N) where MW is a molecular weight of a hydrocarbon fluid molecule, N is a hydrocarbon fluid chain length of that hydrocarbon fluid molecule, and $\sigma$ is the weight fraction of alkanes in the hydrocarbon fluid sample.

13. The method according to claim 12, wherein said relating the hydrocarbon fluid molecular weight distribution to the boiling point distribution comprises solving for $$MW = 42.965 \exp(2.097 \times 10^{-4} BP - 7.78712) \left[\frac{141.5}{(5443 \times MW^{-0.939} + 131.5)}\right] + 2.08476 \times 10^{-3} BP \left[\frac{141.5}{(5443 \times MW^{-0.939} + 131.5)}\right] + BP^{1.26007}\left[\frac{141.5}{(5443 + MW^{-0.939} + 131.5)}\right]^{4.98308}$$

where BP is the boiling point of a hydrocarbon fluid molecule of molecular weight MW.

14. The method according to claim 1, further comprising providing the boiling point distribution as an input to a petroleum thermodynamic model.

15. The method according to claim 1, wherein said applying the NMR signal to the sample comprises applying the NMR signal to the sample at one of a rig site, a transportation pipeline and a refinery facility.

16. The method according to claim 1, further comprising:
displaying the boiling point distribution in a graph where a percent yield is plotted against a boiling point temperature to provide a volume percentage curve and a weight percentage curve.

17. A method for determining a boiling point distribution of a hydrocarbon fluid comprising:
obtaining a sample of the hydrocarbon fluid at a rig site, a transportation pipeline, or a refinery facility;
using an nuclear magnetic resonance (NMR) system, applying an (NMR) signal to the sample and measuring at least one of a resulting translational diffusion signal and a resulting spin relaxation signal;
determining at least one of an NMR translational diffusion distribution and an NMR decay distribution from the at least one of a resulting translational diffusion signal and a resulting spin relaxation signal;
determining a hydrocarbon fluid chain length distribution from the at least one of the NMR translational diffusion distribution and NMR decay distribution;
relating the hydrocarbon fluid chain length distribution to a hydrocarbon fluid molecular weight distribution; and
determining a boiling point distribution for the hydrocarbon fluid by relating the hydrocarbon fluid molecular weight distribution to the boiling point distribution.

18. The method of claim 17, wherein said determining a hydrocarbon fluid chain length distribution comprises solving $D_i = [A(T,p)\langle N \rangle^{-\beta(T,p)}]N_i^{-\nu}$ for $N_i$, where $N_i$ is said hydrocarbon fluid chain length distribution, $D_i$ is said NMR translational diffusion distribution, $\langle N \rangle$ is a weighted average chain size of all molecules in the sample, A and $\beta$ are known coefficients which are a function of temperature T and pressure p, and the exponent $\nu$ is a constant.

19. The method of claim 17, wherein said determining a hydrocarbon fluid chain length distribution comprises solving $T_{,i} = [B(T,p)\langle N \rangle^{-\gamma(T,p)}]N_i^{\kappa}$ for $N_i$, where $N_i$ is said hydrocarbon fluid chain length distribution, $T_{,i}$ is said NMR decay distribution, B and $\gamma$ are known coefficients which are a function of temperature T and pressure p, the exponent $\kappa$ is a constant, and $T_{,i}$ is either a $T_{2,i}$ NMR decay distribution or a $T_{1,i}$ NMR decay distribution.

20. The method of claim 17, wherein said relating the hydrocarbon fluid chain length distribution to a hydrocarbon fluid molecular weight distribution comprises solving for at least one of $MW=(N\times14)+2$ and $MW=\sigma(14N+2)+(1-\sigma)(13N)$ where MW is a molecular weight of a hydrocarbon fluid molecule, N is a hydrocarbon fluid chain length of that hydrocarbon fluid molecule, and $\sigma$ is the weight fraction of alkanes in the hydrocarbon fluid sample, and said relating the hydrocarbon fluid molecular weight distribution to the boiling point distribution comprises solving for $$MW = 42.965 \exp(2.097\times10^{-4}BP - 7.78712)\left[\frac{141.5}{(5443\times MW^{-0.939}+131.5)}\right] + 2.08476\times10^{-3}BP\left[\frac{141.5}{(5443\times MW^{-0.939}+131.5)}\right]$$
$$BP^{1.26007}\left[\frac{141.5}{(5443+MW^{-0.939}+131.5)}\right]^{4.98308}$$

where BP is the boiling point of a hydrocarbon fluid molecule of molecular weight MW.

\* \* \* \* \*